United States Patent

Wythes

[11] Patent Number: 5,994,387
[45] Date of Patent: Nov. 30, 1999

[54] PYRROLIDINYL METHYL INDOLE SALT

[75] Inventor: Martin James Wythes, Sandwich, United Kingdom

[73] Assignee: Pfizer Inc., New York, N.Y.

[21] Appl. No.: 08/952,792

[22] PCT Filed: Apr. 10, 1996

[86] PCT No.: PCT/EP96/01560

§ 371 Date: Nov. 12, 1997

§ 102(e) Date: Nov. 12, 1997

[87] PCT Pub. No.: WO96/36632

PCT Pub. Date: Nov. 21, 1996

[30] Foreign Application Priority Data

May 20, 1995 [GB] United Kingdom ............ 9510223

[51] Int. Cl.$^6$ .................. A01N 43/38; C07D 209/02
[52] U.S. Cl. ................ 514/415; 548/465; 548/468; 548/469
[58] Field of Search .................. 548/465, 468, 548/469; 514/415

[56] References Cited

U.S. PATENT DOCUMENTS 5,039,679  8/1991  Herman ..................... 514/300
5,545,644  8/1996  Macor et al. ............... 514/323

FOREIGN PATENT DOCUMENTS 385422      2/1990  European Pat. Off. .
9206973     4/1992  WIPO .
WO 92/06973 4/1992  WIPO .
9425023     4/1994  WIPO .

OTHER PUBLICATIONS

Berge, et al., *J. Pharm. Sci.* 66(1), 1–19 (1977).

Primary Examiner—Dwayne C. Jones
Attorney, Agent, or Firm—Peter C. Richardson; Paul H. Ginsburg; Grover F. Fuller, Jr.

[57] ABSTRACT

The fumarate salt of (R)-5-(methylaminosulphonylmethyl)-3-(N-methylpyrrolidin-2-ylmethyl)-1H-indole, useful in the treatment of migraine.

4 Claims, 1 Drawing Sheet

PYRROLIDINYL METHYL INDOLE SALT

This application is a 371 of PCT/EP 96/01560, filed Apr. 10, 1996.

This invention relates to the fumarate salt of (R)-5-(methylaminosulphonylmethyl)-3-(N-methylpyrrolidin-2-ylmethyl)-1 H-indole of the structure:

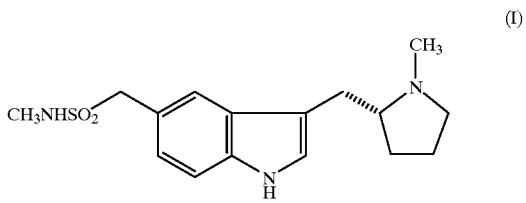

Compound (I) in its free base form is described in Example 5A of WO-A-92/06973. The fumarate salt of (I) has not previously been described, although fumarate salts are mentioned in general terms only in a list of suitable pharmaceutically acceptable acid addition salts in WO-A-92/06973.

We have now found that the fumarate salt of (I) has unexpectedly improved stability to oxidative degradation. Also, and again unexpectedly, it has excellent solubility and solid state stability and is non-hygroscopic.

Accordingly, the present invention provides the fumarate salt of (R)-5-(methylaminosulphonylmethyl)-3-(N-methylpyrrolidin-2-ylmethyl)-3-(N-methylpyrrolidin-2-ylmethyl)-1 H-indole, pharmaceutical compositions containing It, and its use in treating migraine.

The salt can be prepared by the reaction of compound (I) with fumaric acid, typically about 1 equivalent, in a suitable organic solvent or mixture of solvents as is illustrated in the following Example.

It can be formulated and administered to humans to treat migraine and other indications as described in WO-A-92/06973, which is incorporated herein by reference.

EXAMPLE

Figure 1:
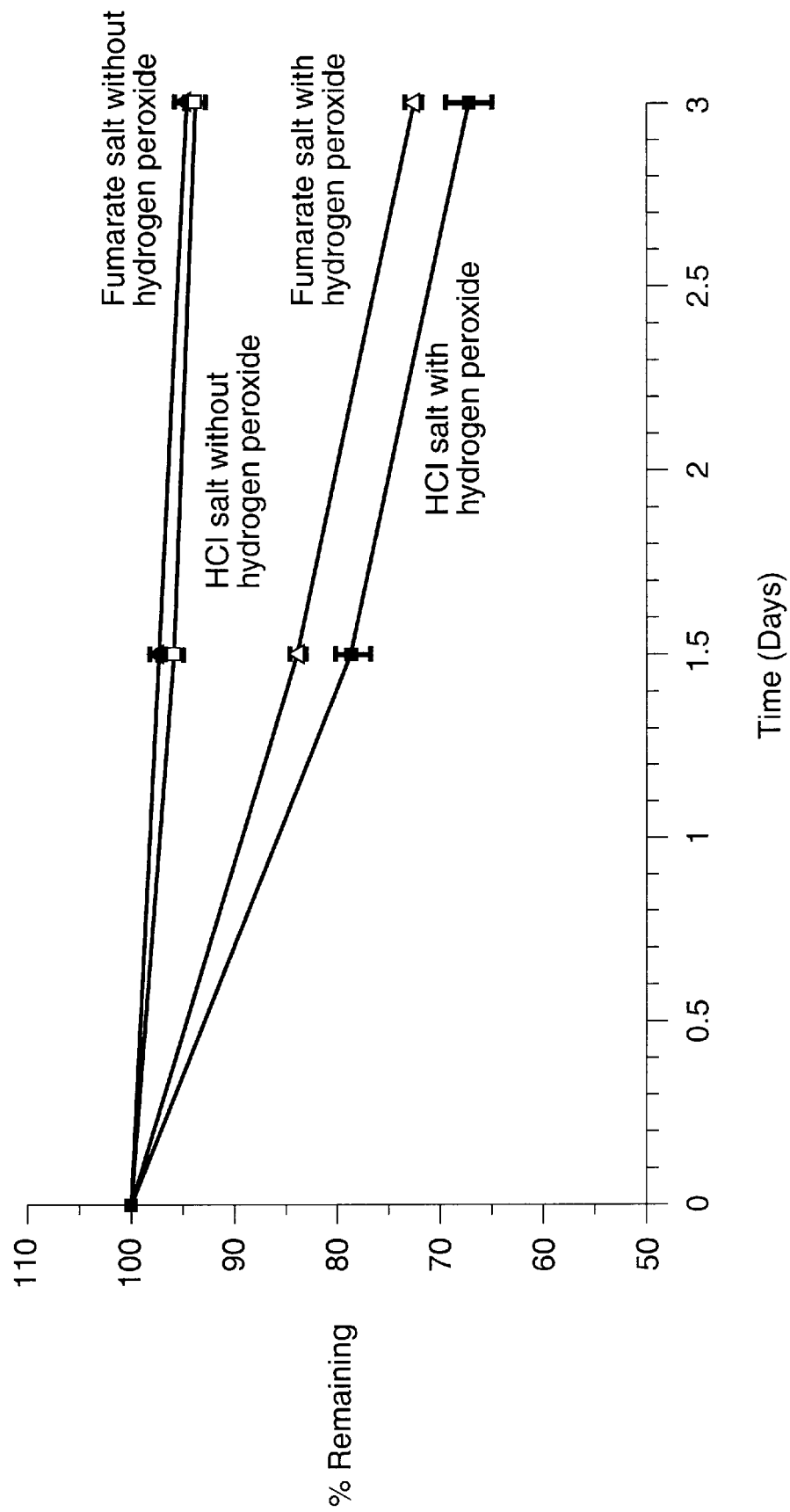
FIG. 1 is a graph of the stability of Compound (I) in 90% PEG 400 at 40° C. with and without oxidative stress (mean±stand. dev., n=3).

(R)-5-(Methylaminosulphonylmethyl)-3-(N-methylpyrrolidin-2-ylmethyl)-1H-indole To a suspension of (R)-5-(methylaminosulphonylmethyl)-3-(N-methylpyrrolidin-2-ylmethyl)-1H-indole (16.25 g, 0.0506 mol) in methanol (81.25 ml) was added, in one portion, fumaric acid (5.87 g, 0.0506 mol) at ambient temperature giving a fine suspension that was filtered and washed with methanol (16 ml). The stirred liquors were heated to reflux and diluted with acetonitrile (50 ml). Solvent was removed by distillation at atmospheric pressure and replaced with acetonitrile up to a vapour temperature of 80° C. During distillation the solution was seeded with (R)-5-(methylaminosulphonylmethyl)-3-(N-methylpyrrolidin-2-ylmethyl)-1H-indole fumarate and a slurry was produced. The slurry was allowed to cool to ambient temperature then granulated at 0° C. for 1 hour. Filtration gave the product (21.45 g, 97%) as off-white crystals, m.p. 159° C. (by DSC). Rf. 0.2 (silica, diethyl ether/ethyl acetate/DEA/MeOH, 10:10:1:1); $[\alpha]_d$+13.17° (c=1,H$_2$O).

Found: C,54.94;H,6.35;N,9.60% $C_{16}H_{23}N_3O_2S;C_4H_4O_4$ requires: C,54.91;H,6.22;N,9.60%

$^1$H-NMR (300 MHz. DMSO-d$_6$): δ=1.50–1.90 (m, 4H), 2.50–2.54 (d, 3H), 2.54–2.60 (s, 3H), 2.62–2.74 (m, 1H), 2.82–2.96 (m, 1H), 3.08 (dd, 1 H), 3.20–3.30 (m, 1H), 4.28–4.36 (s, 2H), 6.48–6.54 (s, 2H) 6.70–6.80 (q, 1H), 7.02–7.12 (d, 1H), 7.16–7.22 (s, 1H), 7.28–7.36 (d, 1H), 7.48–7.56 (s, 1H), 10.86–10.94 (s, 1H).

Saturated solubility of the free base and fumarate salt of Compound (I)

For both the free base and fumarate salt, approximately 50 mg of solid bulk material was accurately weighed into a 1.5 mL plastic "Eppendorf" tube (Sigma). 0.3 mL of water (MilliQ) was then added to the tubes. The tubes were then vortex mixed at 1,300 rpm ("LKB") for 16 hours at room temperature. The supernatant was separated from undissolved material by centrifugation at 13,000 rpm for 20 minutes ("Heraeus Biofuge 13"), then diluted and assayed for Compound (I) by HPLC. This assay used a mobile phase of acetonitrile (20%), water (80%) and trifluoroacetic acid (0.1%) and a 150×4.2 mm "Zorbax SB CN" column at 40° C. with U.V. detection at 220 nm. The results are set out below.

Hygroscopicity

Approximately 10 mg of each of the free base and fumarate salts of Compound (I) were exposed to 8 different relative humidities (RHs) between 0 and 94% at 30° C. in the Surface Measurement Systems Ltd moisture microbalance. The samples were allowed to reach equilibrium at each of these RHs and the change in weight from the initial value when the sample was first placed in the balance was calculated. The data was used to construct the moisture sorption isotherms for the materials. The hygroscopicity of the materials was compared by calculating the moisture uptake at 90%RH, which was as follows:

| Bulk form | Solubility (mg/mL) | Hygroscopicity at 30° C. and 90% RH (% w/w) |
| --- | --- | --- |
| Free base | 0.12 | 0.2 |
| Fumarate salt | 67.5 | 0.2 |

Increased solubility of the fumarate salt in water simplifies aqueous solution formulation and aids dissolution of solid dosage forms. The increased aqueous solubility of the fumarate salt was not accompanied by increased hygroscopicity of the bulk form [which potentially could lead to reduced bulk stability].

Oxidative stability of Compound (I)

Soft gelatin capsule formulations are an attractive delivery system for Compound (I) as they improve in vivo dissolution and content uniformity on manufacture. The compound (I) can be formulated as a liquid fill soft gelatin capsule. However, oxidative degradation often limits the shelf life of such formulations. PEG 400 is representative of a typical liquid fill diluent used for such a purpose. The following study was designed to determine whether oxidative degradation occurs with Compound (I) in such a formulation, and whether the fumarate salt provides protection against oxidative degradation. 1 mg/mL solutions of Compound (I) as the free base, Compound (I) as the hydrochloride salt and Compound (I) as the fumarate salt were prepared in 90% PEG 400 (BDH) and 10% water (Milli-Q). 10% water was added to the formulations to mimic the ingress of water from the soft gelatin capsule shell. The free base was not very soluble in the formulation which prohibited further investigation of this bulk form. However, for ease of solution preparation, the hydrochloride salt was used instead.

Hydrogen peroxide (BDH) to a final concentration of 0.3% w/w was added to the formulations to provide an oxidative stress. A control formulation without hydrogen peroxide was also used in the study. 1 mL of each formulation was sealed into 2 mL HPLC vials ("Cromacol") and placed in a thermostated oven at 40° C. Samples were taken at 1.5 and 3 days and stored frozen (−20° C.) prior to assay. The samples were diluted and analysed using the stability indicating HPLC assay as described above. Degradation was expressed as % Compound (I) remaining.

As is shown in FIG. 1, the stability study demonstrated that both salt forms of Compound (I) were relatively stable in the PEG 400 formulation in the absence of oxidative stress. When however an oxidative stress was applied to the formulation by the addition of hydrogen peroxide, a significant increase in degradation was observed. This demonstrates that oxidative degradation can occur in the softgel formulations of Compound (I) with a resulting impact on formulation shelf-life. Thus, bulk forms with improved stability in an oxidative environment will aid formulation in soft gelatin capsules.

The degradation rate of the fumarate salt was significantly lower (analysis of variance p<0.001) than the hydrochloride at both time points. The antioxidant properties of the fumarate salt offers significant protection against degradation in the formulation and aids its formulation in softgel vehicles.

As far as we are aware, there are no previous reports in the literature regarding superior oxidative stability for fumarate salts.

Solid-State Stability

Approximately 1 mg of each of the free base, hydrochloride, hydrobromide and fumarate salts of Compound (I) were accurately weighed into small glass vials. These were stored for 9 weeks at each of 4° C./ambient humidity, 40° C./ambient humidity, 40° C./75% RH and 50° C./ambient humidity. The samples were then assayed using the following stability indicating HPLC method. A mobile phase consisting of 0.05 M potassium dihydrogen orthophosphate adjusted to pH2 with phosphoric acid (90%) and acetonitrile (far UV) (10%), was pumped through a "Zorbax SB-CN" 150×4.6 mm column (40° C.) at a flow rate of 1 ml/min with UV detection at 225 nm.

The samples with the exception of the free base were prepared by dissolving them in the mobile phase in a 25 ml volumetric flask. The free base was dissolved in a few drops of methanol before diluting with the mobile phase.

The stability of the samples was quantified by investigating the appearance of new peaks in the chromatograms of stored samples and the increase in peaks present compared to control samples stored at 4° C. The degradation expressed in this way for the free base and the fumarate salt stored at 50° C. is shown in the Table below. Similar trends were observed at the lower temperature storage conditions. It can be seen from data that the fumarate salt had not degraded at all after 9 weeks 50° C., whereas the free base showed measurable degradation with the appearance of 4 new drug related peaks. Therefore, the fumarate salt is the most stable in the solid state and has a suitable bulk form shelf-life for pharmaceutical development.

TABLE

Compound (I): Bulk Stability Data after 9 weeks at 50° C.

| Relative Retention Time | % Degradation (% peak area @ 50° C.–% peak area @ 4° C.) | |
|---|---|---|
|  | Free Base | Fumarate Salt |
| 0.40 | 0.05 | — |
| 0.59 | — | 0.00 |
| 0.60 | 0.01 | — |
| 0.64 | 0.02 | 0.00 |
| 0.77 | — | — |
| 0.85 | — | — |
| 0.91 | 0.02 | — |
| 1.00 | Compound (I) main band | |
| 1.35 | 0.02 | 0.00 |
| 1.66 | 0.17 | — |
| 1.93 | 0.03 | — |
| total increase in % peak area | 0.32 | 0.00 |

— No peaks present at this relative retention time
Figure bold and underlined indicates a new peak has appeared.

The hydrochloride and hydrobromide salts referred to above were prepared conventionally, for example, to prepare the hydrochloride salt, a solution of Compound (I) in ethanol was treated at 65° C. with ca. 1 equivalent of conc. HCl and allowed to cool. Removal of the solvent in vacuo and recrystallisation of the residual froth from absolute ethanol gave the hydrochloride salt.

The hydrobromide salt was prepared substantially as above except 48% HBr was used.

I claim:

1. The fumarate salt of (R)-5-(methylaminosulphonylmethyl)-3-(N-methylpyrrolidin-2-ylmethyl)-1H-indole.

2. A pharmaceutical composition comprising the fumarate salt as claimed in claim 1 and a pharmaceutically,acceptable diluent or carrier.

3. A method of treating migraine in a human comprising administering to said human an effective amount of a fumarate salt as claimed in claim 1.

4. A process for preparing the fumarate salt of (R)-5-(methylaminosulphonylmethyl)-3-(N-methylpyrrolidin-2-ylmethyl)-1-H-indole, comprising reacting (R)-5-(methylaminosulphonylmethyl)-3-(N-methylpyrrolidin-2-ylmethyl)-1H-indole with one equivalent of fumaric acid.

* * * * *